US006074837A

United States Patent [19]

Procyk et al.

[11] Patent Number: 6,074,837

[45] Date of Patent: Jun. 13, 2000

[54] ASSAYS USING A SOLUBLE FIBRIN-LIKE MONOMER

[75] Inventors: Roman Procyk, Westfield; Bohdan J. Kudryk, Little Ferry, both of N.J.

[73] Assignee: New York Blood Center, Inc., New York, N.Y.

[21] Appl. No.: 08/468,460

[22] Filed: Jun. 6, 1995

Related U.S. Application Data

[63] Continuation of application No. 08/308,482, Sep. 19, 1994, abandoned, which is a continuation of application No. 07/946,826, Sep. 17, 1992, abandoned, which is a continuation of application No. 07/572,189, Aug. 23, 1990, abandoned.

[51] Int. Cl.[7] .............................. C12Q 1/56; G01N 33/53

[52] U.S. Cl. ............................ 435/13; 435/7.1; 435/7.71; 435/68.1; 436/69; 530/382; 530/407

[58] Field of Search .............................. 435/7.1, 13, 7.71, 435/68.1; 436/69; 530/381, 382, 407

[56] References Cited

U.S. PATENT DOCUMENTS

| | | | |
|---|---|---|---|
| 4,429,040 | 1/1984 | Becker et al. | 435/13 X |
| 4,647,554 | 3/1987 | Jolles et al. | 435/68.1 |
| 4,818,690 | 4/1989 | Paques | 435/13 |

FOREIGN PATENT DOCUMENTS

| | | | |
|---|---|---|---|
| 0094720 | 11/1983 | European Pat. Off. . | |
| 0346741 | 12/1989 | European Pat. Off. | 435/13 |
| 8605814 | 10/1986 | WIPO | 435/13 |
| 8606489 | 11/1986 | WIPO | 435/13 |
| 8900005 | 1/1989 | WIPO . | |

OTHER PUBLICATIONS

Procyk, R. et al, "Disulfide Bond Reduction in Fibrinogen: Calcium Protection and Effect on Clottability", *Biochemistry*, 1990, 29, pp. 1501–1507.

Roman Procyk et al., Biochemistry, 1992, 31 2273–2278.

Clin. Chem. 32/3, 482–485 (1986).

*Primary Examiner*—Carol A. Spiegel

*Attorney, Agent, or Firm*—Sprung Kramer Schaefer & Briscoe

[57] ABSTRACT

An assay method that requires a soluble fibrin monomer or a soluble fibrin monomer reagent as one of the components of the assay. The reagent is a fibrin-like material having a solubility and stability similar to fibrinogen in that it remains soluble and stable at physiological conditions at a concentration employed in the assay in the absence of fibrin polymerization inhibitors or reagents for maintaining solubility.

7 Claims, 5 Drawing Sheets

ASSAYS USING A SOLUBLE FIBRIN-LIKE MONOMER

This application is a continuation, of application Ser. No. 08/308,482, filed Sep. 19, 1994 now abandoned, which is a continuation, of application Ser. No. 07/946,826, filed Sep. 17, 1992 now abandoned.

BACKGROUND OF THE INVENTION

1. Field of the Invention

The present invention concerns the use of a modified form of fibrinogen as a fibrin-like substance in immunological and biochemical assays and procedures that require soluble fibrin monomer, soluble fibrin or fibrin.

2. Background Information

The soluble plasma protein fibrinogen is the precursor from which insoluble fibrin networks of blood clots form. This process is well known. Fibrinogen is activated by thrombin and the activated fibrinogen polymerizes to form the clot. Activation occurs through cleavage of the fibrinogen Aα15Arg-16Gly bond, which releases the amino-terminal fibrinopeptide A, and the Bβ14Arg-15Gly bond, which releases the amino-terminal fibrinopeptide B. It is believed that the new amino-termini act as polymerization domains that interact with complementary polymerization sites at the carboxy-terminal region of neighboring molecules, thus enabling activated fibrin monomers to associate by aligning in a double-stranded protofibril. Protofibrils grow in length and associate laterally to form thicker fibrin fibers. These fibers also associate to form thicker fibrin strands of a clot network.

The formation of fibrin in vivo influences many physiological processes related to hemostasis, such as the activation of the clot stabilizing enzyme (factor XIII), the control of fibrinolysis and endothelial cell secretion. Laboratory studies of these processes typically involve analysis of the phenomenon in the presence of fibrin. The stimulatory (or required) effect of fibrin on the activity is documented. Since fibrin polymerizes, a process which, in neutral buffers, is accompanied by formation of a precipitate or aggregate, the use of fibrin in biological and clinical assays has heretofore been limited. A solubilized form of fibrin, or fragments of fibrin formed by proteolytic or chemical degradation of fibrin have been used in most studies, since the clotted form of fibrin is difficult to handle and cannot be easily quantitated.

Solubilized fibrin is routinely prepared from clotted fibrin by dissolving the clot in buffers containing high concentrations of chaotropic denaturing reagents, e.g., urea, guanidine hydrochloride, sodium bromide or acid (e.g., acetic acid). Only fibrin that has not been stabilized by factor XIII can be dissolved in buffers containing any of these agents. Fibrin solubilized by such methods remain in solution only in the presence of the acid or chaotrope containing buffers. These conditions destroy the biological properties of most other proteins, enzymes and cells of interest, and for this reason acid or chaotrope-treated soluble fibrin has only limited applications.

Soluble fibrin is also prepared by converting fibrinogen to fibrin in the presence of polymerization inhibitors, e.g., the peptide Gly-Pro-Arg-Pro (Laudano, A. P., Cottrell, B. A. and Doolittle, R. F., (1983) Synthetic Peptides Modeled on Fibrin Polymerization Sites, *N.Y. Acad. Sci.*, Vol. 408, pp. 315–329 and reference cited within) or fibrinogen fragment D. In this case, the activation of fibrinogen usually is carried out only on the Aα-chain using snake venom enzymes, e.g., batroxobin (Wiman, B. and Ranby, M., (1986), Determination of Soluble Fibrin in Plasma By a Rapid and Quantitative Spectrophotometric Assay, *Thromb. and Haemostas,* 55, 189–193). Only one set of polymerization sites is activated by this method and a single polymerization inhibitor can be used to effectively prevent the aggregation of the fibrin, e.g., DESAFIB™, from American Diagnostica, Inc., Greenwich, Conn. The fibrin remains soluble in physiological buffers, however, only if there is a suitable high concentration of the polymerization inhibitor present in the solution. Fibrin precipitation occurs if the concentration of the polymerization inhibitor is lowered by dilution.

Because of the difficulty of solubilizing fibrin under physiological conditions, any new form of fibrin, or a substance with the properties of fibrin, that does not require special conditions for maintaining solubility would be very useful, especially for use in biochemical and immunological assays that require fibrin monomer or soluble fibrin.

Procyk and Blombäck have described the preparation of modified forms of fibrinogen by disulfide bond reduction which have a prolonged clotting time when treated with thrombin (Procyk, R. & Blombäck, B. (1990) Disulfide Bond Reduction in Fibrinogen: Calcium Protection and Effect on Clottability. *Biochemistry* 29, 1501–1507). The modified fibrinogen was prepared by mild reduction in the absence of calcium ions and formed a gel only by a mechanism involving oligomerization and crosslinking catalyzed by factor XIII. Until now, however, nothing was known about the properties of this material, its stability, solubility, or suitability in applications requiring soluble fibrin or soluble fibrin monomers.

Applicants have discovered that the modified fibrinogen has substantial biochemical and immunological equivalency to fibrin and use this discovery to invent useful applications of the modified fibrinogen in assays and procedures. This invention has special applications in diagnostic determinations of coagulation and/or fibrinolysis which require a form of soluble fibrin or fibrinogen fragments for the assay procedure.

DEFINITIONS $A_{490}$: absorbance at 490 nanometers

Arg: arginine

ATU: Antithrombin units

Bβ15–21: a peptide containing the amino acid sequence of the fibrinogen Bβ-chain from residues number 15–21

Bβ15–42: a polypeptide containing the amino acid sequence of the fibrinogen Bβ-chain from residues number 15–42

Bβ15–118: a polypeptide containing the amino acid sequence of the fibrinogen Bβ-chain from residues number 15–118

Bβ15–461: a polypeptide containing the amino acid sequence of the fibrinogen Bβ-chain from residues number 15–461

Cys: cysteine desAA-fibrin: fibrin that lacks both fibrinopeptides A (fibrin I)

desAABB-fibrin: fibrin that lacks both fibrinopeptides A and B (fibrin II)

DTT: dithiothreitol

E (1%, 1 cm): extinction coefficient

EDTA: ethylenediaminetetraacetic acid

ELISA: enzyme linked immunosorbent assay

Fibrinin: fibrin-like monomer as described in Examples 1–3 hereinbelow fmol: femtomole Gly: glycine
M: molar
mm: millimolar
NIH: National Institutes of Health
nm: nanometer
PAI: plasmin activator inhibitor
pmol: picomole
Pro: proline
RIA: radioimmunoassay
(T)N-DSK: the thrombin-treated amino-terminal cyanogen bromide generated fragment of human fibrinogen, containing the polypeptide fragments (Aα16–51, Bβ15–118, $\gamma$1–78)$_2$
TNE: tris-saline-EDTA buffer
t-PA: tissue-plasminogen activator
Tris: Tris(hydroxymethyl)aminomethane
U: Unit
$\mu$C: microcurie

SUMMARY OF THE INVENTION

It is an object of the present invention to provide assays that require a soluble fibrin or soluble fibrin monomer reagent as one of the components of the assay.

The above object, as well as other objects, aims and advantages are satisfied by the present invention.

The present invention concerns an assay method that requires a soluble fibrin or a soluble fibrin monomer reagent as one of the components of the assay, wherein the reagent is a fibrin-like material having a solubility and stability similar to fibrinogen in that it remains soluble and stable under physiological conditions at a concentration employed in the assay, e.g., 0.08 mg/ml to 15 mg/ml, in the absence of fibrin polymerization inhibitors or reagents for maintaining solubility.

Assays methods include, for example, assays for the quantitative determination of (1) soluble fibrin monomers, (2) plasmin activator inhibitor activity, (3) tissue-plasminogen activator activity in human plasma and (4) immunoassays.

A fibrin-like material for use in the present invention is preferably a material that remains soluble and stable in physiological buffers, and under conditions that are appropriate for the solubility and stability of fibrinogen, including a pH of 3 to 10 and a wide range of concentrations, i.e., from as low as 0.08 mg/ml to as high as 15 mg/ml, without the requirement of any reagents for maintaining solubility or fibrin polymerization inhibitors.

Surprisingly, it has been found that such fibrin-like material ("Fibrinin") has immunological and biochemical properties that are similar to the other types of solubilized fibrin and can therefore be used in the same capacity as these other varieties. These applications include use for different types of immunoassays and also in tests for the quantitative determination of soluble fibrin monomers, plasmin activator inhibitor ("PAI") activity or tissue-plasminogen activator (t-PA) activity in human plasma.

The fibrin-like soluble reagent that can be employed in the present invention is produced by a process which leads to a modification of the structure of fibrinogen such that activation of the modified fibrinogen with thrombin does not lead to clotting. The modification is based on the cleavage of several disulfide bonds in fibrinogen with a low amount of reducing reagent. The cleavages lead to a slight disruption of the protein's structure that changes some of the protein's properties. On exposure to thrombin, or other clotting enzymes, the modified fibrinogen interacts with such enzymes in a similar fashion to unmodified fibrinogen in terms of the release of fibrinopeptides. However, the modified fibrinogen does not polymerize and remains soluble in the solution even though the fibrinopeptides are released.

The fibrin-like soluble fibrin reagent can be produced by a process that comprises (a) subjecting the protein fibrinogen to reduction to cleave a limited number of the protein's disulfide bonds in the absence of divalent cations, (b) blocking the cleaved bonds using an agent which irreversibly blocks the thiol groups of the free cysteines formed during the reduction by contacting the resultant fibrinogen from (a) with a blocking agent, (c) contacting the resultant fibrinogen from (b) with the enzyme thrombin to cleave the amino termini of the resultant protein, whereby to release fibrinopeptides A and B and (d) stopping the action of the enzyme by adding a suitable inhibitor or by separating the enzyme from the soluble fibrin-like monomer of (c).

BRIEF DESCRIPTION OF THE DRAWINGS

For the purpose of illustrating the invention there is shown in the drawings forms which are presently preferred. It is to be understood, however, that the present invention is not limited to the precise arrangements and instrumentalities depicted in the drawings.

DETAILED DESCRIPTION OF THE INVENTION

Figure 1:
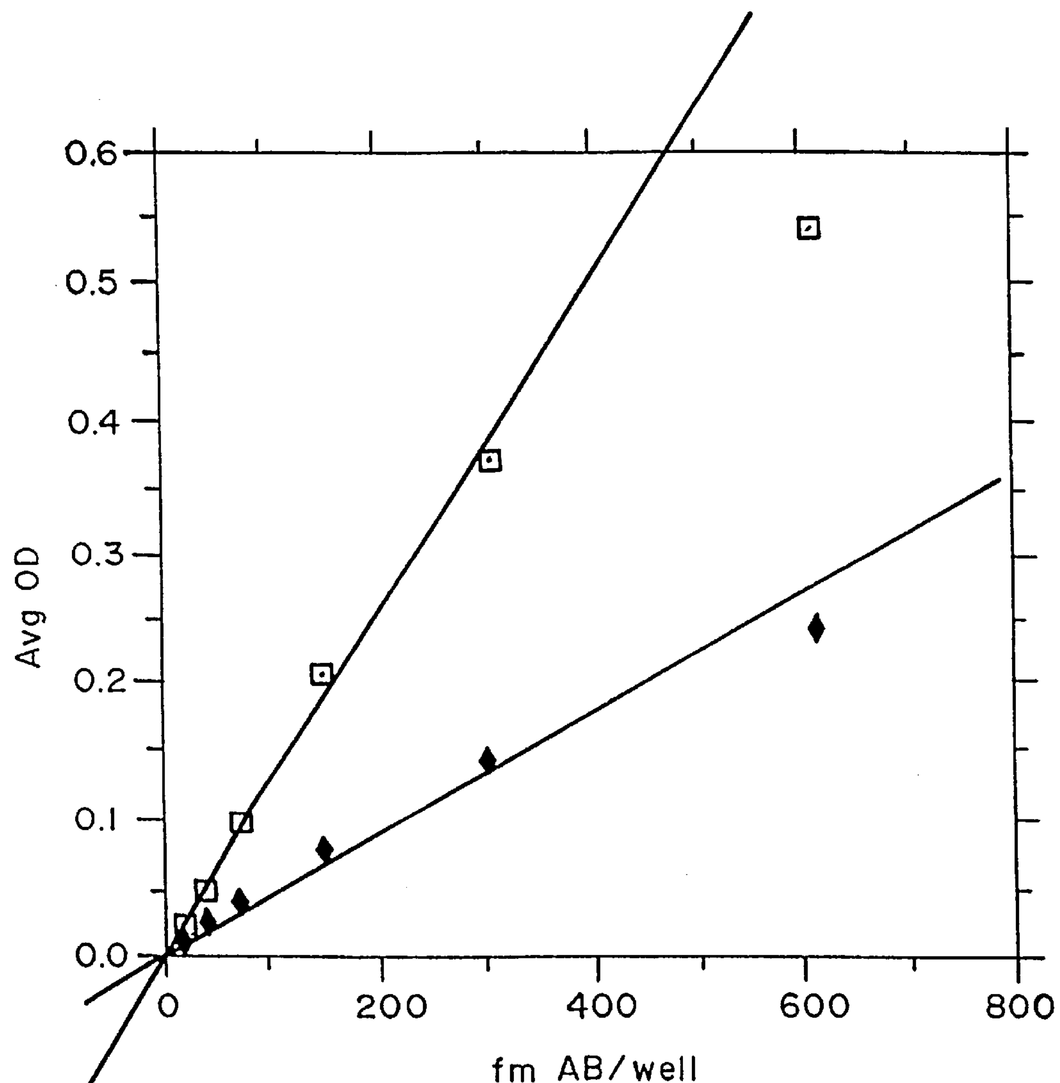
FIG. 1 is a graph depicting binding of a monoclonal antibody against fibrin (antibody T2G1) to plastic wells coated with either acid solubilized fibrin or the soluble fibrin-like monomer produced according to the invention.

A soluble and stable reagent with some of the biochemical properties of fibrin and that can be employed in the present invention is prepared essentially according to Procyk and Blombäck (Procyk, R. & Blombäck, B., (1990) Disulfide Bond Reduction in Fibrinogen: Calcium Protection and Effect on Clottability, *Biochemistry* 29, 1501–1507) with modifications designed to simplify the process.

Fibrinogen is modified by first subjecting the protein to a limiting (partial) reduction. The reduction is conducted with a concentration of fibrinogen ranging between about 3 to 25 micromolar with a preferred concentration being 20.6 micromolar. A slightly elevated temperature is required, i.e., 30 to 40° C., such as 37° C. The reduction is carried out under non-denaturing conditions, e.g., in physiological buffers, buffered saline, buffers of suitable ionic strength and pH, e.g., a pH of 7.2 to 8.3, such as not to cause the precipitation of fibrinogen. A low amount of reducing reagent is used, e.g., up to 0.25 millimole reducing reagent per nanomole fibrinogen, depending on reduction potential of the reducing reagent. The reducing reagent can be one composed of, for example, thiols, such as dithiothreitol, 2-mercaptoethanol, 3-mercaptopropionate, 2-aminoethanethiol or other similar reagents; reducing agents such as sodium borohydride, etc. or biological reducing reagents, such as glutathione, cysteine or thioredoxin. The reduction is conducted in the absence of divalent cations and this can be achieved by having present in the reaction mixture a suitable concentration, e.g., 0.1 to 10 mM divalent cation chelators (e.g., ethylenediaminetetraacetic acid, ethyleneglycol-bis-(β-aminoethyl ether) N,N,N',N'-tetraacetic acid) or other chelators that will bind calcium and other divalent cations and concentrations that will not cause the precipitation of the protein in solution.

The reduction time is selected to allow almost complete cleavage of the susceptible disulfide bonds, which in most cases, depending on choice of fibrinogen concentration and reducing reagent, is ½ to 1½ hours and preferably up to about 1 hour.

The above described partial reduction is followed by blocking the thiol group of the free cysteines formed during reduction with a blocking reagent, e.g., iodoacetic acid, iodoacetamide, N-ethylmaleimide, or other thiol blocking reagents that will not lead to the precipitation of the protein product.

The blocking is conducted at a temperature of 20 to 27° C. for a period of time of ½ to 2 hours. The concentration of blocking reagent needed varies, depending on whether the reducing reagent is removed from the reaction mixture prior to addition of the blocking reagent (see Examples 1 and 2) and can be between 1.5 to 40 millimolar.

The recovered fibrinogen is treated to alter the amino termini of the protein, which includes the release of the fibrinopeptides A and B. This can be done enzymatically, in physiological buffers, such as tris-buffered saline, in the absence of divalent cations such as calcium. The protein is reacted with clotting enzymes such as thrombin, batroxobin or other snake venoms, or enzymes with similar proteolytic specificity. The treatment is conducted at a temperature of 20° to 27° C., preferably at room temperature, using sufficient enzyme, e.g., 0.2 to 3 NIH units of thrombin or equivalent to release at least greater than 99% of the fibrinopeptide B from the fibrinogen. This can be carried out with the modified fibrinogen at a concentration of 3 to 12 micromolar, preferably 8.8 micromolar and using thrombin at 0.5 NIH units per mL with an incubation of the reaction mixture for 1.5 to 3 hours, preferably 2 hours.

The activity of the added enzyme can be terminated by adding an appropriate enzyme inhibitor in excess. In the case of thrombin, the inhibitor hirudin is suitable (see Examples 1 and 2). Alternatively, the enzyme can be removed from the reaction mixture by an affinity-chromatography technique (see Example 3), or by selectively precipitating the fibrinogen with an ethanol-glycine solution, or with salts such as ammonium sulfate. In another embodiment, the enzyme can be immobilized by a variety of chemical or physical means (e.g., coupled to SEPHAROSE (agarose) beads (Pharmacia, N.J.) by widely practiced methods involving agents such as cyanogen bromide, carbodiimide, etc.) and the modified fibrinogen exposed to give the desired modification of the amino-terminal ends of the modified fibrinogen. The final product, provisionally called "Fibrinin", is a form of fibrin that does not clot and remains fully soluble. Several procedures for preparing Fibrinin, including modifications, are given in Examples 1–4 hereinbelow.

Preparations of Fibrinin are stable and soluble in physiological buffers that are used in clinical and biological assay systems, such as normal saline buffered with any of the typical buffering agents, e.g., Tris (tris[hydroxy-methyl] aminomethane); phosphate; barbital and others. Biological buffers having an ionic strength in the range of normal saline (0.15) are also suitable and include: ACES (2-[(2-amino-oxoethyl)-amino]ethanesulfonic acid); PIPES (piperazine-N,N'-bis[2-ethanesulfonic acid]); MOPS (3[N-morpholino] propanesulfonic acid; bis-tris propane (1,3bis[tris (hydroxymethyl)methyl-amino]propane); BES (N,N-bis[[2-hydroxyethyl]-2-aminoethanesulfonic acid); HEPES (N-[2-hydroxyethyl]piperazine-N'-[2-ethanesulfonic acid]); imadazole and others. Although the physiological pH is 7.4 and this is the preferred pH for storing and for use of Fibrinin, the acceptable useful range of pH, as far as is known, is between 6.5–8.5, even though the material is soluble in a pH range of 5.5–10.0, as is fibrinogen. The stability and solubility of preparations of Fibrinin do not differ from those of fibrinogen, and therefore Fibrinin can be handled in a manner as would be suitable for fibrinogen. It is practical to store Fibrinin at 4° C. at a concentration of 1 to 15 mg/mL, with the preferred concentration being 3–5 mg/mL. As such, Fibrinin can be used by diluting a stock solution with a buffer or solution specific to a particular assay or protocol that will give the desired concentration (which can be measured according to the procedure in Example 1).

The immunological properties of Fibrinin that are similar to those of native fibrin are useful for various types of immunoassays that require a fibrin antigen in soluble form. This is especially true for assays that need the fibrin antigen in physiological buffers or biological fluids, such as plasma or blood, i.e., in non-denatured form, in the absence of denaturing agents typically used for solubilizing fibrin such as urea, guanidine or acids. Fibrin, solubilized in any of the just cited agents, cannot be used for immunologic assays. However, this becomes possible with Fibrinin, which was discovered to have immunological properties similar to those of native fibrin. For example, the amino-terminal region of the β-chain of Fibrinin is immunologically indistinguishable from native fibrin and therefore Fibrinin can be used as a fibrin standard in classical direct binding assays or classical direct or indirect competition ELISA or in RIA measuring fibrin or fibrin degradation products.

For the direct type of binding assay according to the invention, an antibody reacting with epitopes on fibrin or fibrin degradation products (such as the plasmin derived amino-terminal fragment of fibrin) that has a reporting group attached to it (such as a radionuclide like 125-iodine or a color generating reagent like the enzyme horseradish peroxidase) would be used to bind to plastic wells of a microtiter plate in which some of the wells have been coated with samples to be analyzed (i.e. plasma, etc.) and others with Fibrinin. The wells coated with Fibrinin would be used as positive controls, since the Fibrinin bound to the wells would contain fibrin-specific epitopes that the antibody would recognize and bind.

For classical direct or indirect competition ELISA according to the invention, Fibrinin has application as antigen bound to wells of microtiter plates (as in the direct binding assays described above) or as competing antigen in solution, i.e. standard in competition assays, etc. For these assays the wells of a microtiter plate would be coated with a substance containing fibrin-related epitopes to which antibody is available and Fibrinin would be appropriate for this use. Serial dilutions of samples such as plasma or mixtures containing unknown amounts of fibrin-related material such as unpolymerized fibrin molecules (soluble fibrin monomer) or fibrin degradation products that possess an epitope to which antibody is available would be mixed with a constant amount of antibody. The concentration of sample at all dilutions should be such as to obtain excess of antibody. This would mean that after all of the sample had bound to antibody, the excess unreacted antibody left would be free to interact with the plastic coated antigen in the wells. Likewise, a stock solution of Fibrinin of known concentration (determined spectrophotometrically or by any of the readily available laboratory assays for protein quantitation) would be serially diluted and also mixed with the constant amount of the antibody. After incubation of the sample to allow for an equilibrium to be reached, all of the mixtures would be transferred to the plastic wells and the fraction of antibody that would be unassociated with sample would bind to the antigen coating the well. In the direct assay, the amount of antibody (previously labeled with horseradish peroxidase) bound would be estimated by color change of substrate-dye. In the indirect assay, specifically bound antibody would be detected with a peroxidase-conjugated second antibody directed against the first antibody (see Example 5).

Fibrinin can also be useful in sandwich type ELISA assays. Wells of a microtiter plate would be coated with a fibrin specific antibody. A stock solution of Fibrinin of known concentration would be serially diluted and applied to the wells to provide data for constructing a standard curve. Samples, such as plasma, would also be serially diluted and applied to other wells. Specifically bound Fibrinin or sample would be detected with a second general antibody (a polyclonal, or a monoclonal different from the one coating the wells) that would be peroxidase-conjugated or tagged such as to be readily detected by methods readily availabe (radiolabeling, second peroxidase-conjugated antibody, etc.).

For RIA competitive based assays according to the invention, Fibrinin has useful applications in that it can be radiolabeled and mixed with sufficient amount of an antibody directed against fibrin and sample and then processed as for RIA. This would entail separation of antibody bound radiolabeled Fibrinin (or sample) from unbound species and measuring the radioactivity of the bound fraction (see Example 6). Because soluble fibrin and monomeric fibrin cannot be prepared under physiologic conditions, or without the excessive use of polymerization inhibitors, these types of assays based on a soluble form of fibrin antigens had to rely on fragments of fibrin or purified oligopeptides containing the epitope of interest in lieu of actual soluble fibrin containing the antigen. The use of Fibrinin allows the development of these types of assays. Fibrinin is also useful for any type of ELISA or RIA involving monoclonal antibodies with specificities for conformational epitopes that would be similar to those on fibrin or fibrin degradation products.

Another hitherto unknown property of Fibrinin that is useful is its ability to stimulate t-PA (tissue plasminogen activator) activity in the conversion of plasminogen to plasmin. The stimulation of t-PA by Fibrinin is as effective or even exceeds that of known fibrin-based stimulators, such as DESAFIB™ (des-AA-fibrinogen) or FCB-2 fibrinogen fraction (both from American Diagnostica, Inc., Greenwich, Conn.). Therefore, Fibrinin is useful for the determination of t-PA activity in various types of assays, for example, those based on the amidolytic activity of plasmin. These include assays for the determination of t-PA in human plasma which use the chromogenic substrate S-2251 (Kabi Diagnostica, Molndal, Sweden) (Example 8). The assays can be carried out by adding plasminogen, diluted test plasma or standards containing known amounts of t-PA, Fibrinin (as t-PA stimulator) and chromogenic substrate in a tube, and incubating the contents for some time. Plasmin, which is generated from the plasminogen in proportion to the available amount of t-PA in the sample, will act on the chromagenic substrate to release a p-nitroaniline group, which leads to a change in absorbance at 405 nm. The development of color in the sample can be stopped at a chosen time by adding acetic acid and the end point (final color) measured spectrophotometrically. Alternatively, the reaction can take place in cuvettes inside a spectrophotometer recording the change in absorbance with time. The rate of color change (e.g., slope of a plot of absorbance vs. time squared) would be related to the amount of t-PA in the sample. These assay methods are adaptable to: micro-type analysis using microtiter plates; bioimmunoassays which employ both an immunological technique to capture t-PA (or a complex containing t-PA) and a chromogenic type assay to determine the activity of the captured t-PA and also to centrifugal analyzers. The usefulness of Fibrinin for such assays is that it is simple to prepare, stable, soluble and compatible with plasma and the dilution buffers used in these types of assays, and that the effective concentration of Fibrinin needed to bring about sufficient change in absorbance is similar to that of other t-PA stimulators (Example 8).

The ability of Fibrinin to stimulate t-PA activity in the conversion of plasminogen to plasmin is also useful for other types of assays such as in the determination of fibrin monomer concentration in plasma. Typically the amount of fibrin monomer in a sample of plasma is determined by adding to the sample an amount of plasminogen, t-PA and chromogenic substrate S-2390 (Kabi Diagnostica, Molndal, Sweden). The fibrin monomer present will stimulate the t-PA, which will in turn facilitate the conversion of the plasminogen to plasmin. The amidolytic activity of the generated plasmin on S-2390 (i.e. leading to the release of p-nitroaniline and color change that is detected at 405 nm) is determined spectrophotometrically and correlated to the concentration of fibrin monomer, based on a standard curve, which is obtained by adding various amounts of Fibrinin to freshly thawed normal human plasma (see Example 7).

The ability of Fibrinin to stimulate t-PA activity in the conversion of plasminogen to plasmin is also useful for the determination of plasminogen activator inhibitor (PAI) activity in human plasma. Plasminogen activator inhibitor is important for the regulation of fibrinolysis and is relevant in many clinical situations such as venous thrombosis, myocardial infarction, sepsis, pregnancy and diabetes. Plasminogen activator inhibitor activity is routinely measured by assaying the amount of free t-PA left after mixing a sample with an unknown concentration of PAI with a known concentration of t-PA, with the t-PA concentration being in excess of the general anticipated concentration of PAI. The residual t-PA is measured by an assay as in Example 7 or 8, i.e., quantitating the activity of t-PA left. Fibrinin is very suitable for this purpose and for any general application involving stimulation of t-PA activity in the conversion of plasminogen to plasmin. For example, having properties that stimulate t-PA conversion of plasminogen to plasmin, Fibrinin may be employed for standardization and characterization of various forms of t-PA, including recombinant t-PAs, or for discrimination between t-PA and urokinase (e.g., Karlan, B. Y., Clark, A. S. and Littlefield, B. A., (1987) "A Highly Sensitive Chromogenic Microtiter Plate Assay for Plasminogen Activators Which Quantitatively Discriminates Between the Urokinase and Tissue-Type Activators", *Biochem. Biophys. Res. Comm.,* 142, 147–154).

The t-PA stimulatory activity of Fibrinin that is desirable can also be obtained, albeit with slightly diminished effectiveness, without altering the amino termini of the partially reduced fibrinogen, as called for in the last steps in its Fibrinin preparation, i.e., the process which includes removal of fibrinopeptides A and B (Examples 1–3). This abridged process leads to the preparation of Fibrinin-like material and is still based on the cleavage of several disulfide bonds in fibrinogen with a low amount of reducing reagent and leads to a slight disruption of the protein's structure that allows it to stimulate t-PA activity more so than unmodified fibrinogen (see Example 8, FIG. 4, curve 3).

The t-PA stimulatory activity of Fibrinin that is desirable can also be enhanced by oligomerization (Example 9). The latter can be done enzymatically by the addition of a crosslinking enzyme, such as plasma factor XIII or tissue or liver transglutaminase, or chemically by the addition of chemical crosslinking reagents, such as glutaraldehyde, or similar reagents (Example 4).

The invention will now be described with reference to the following non-limiting examples.

EXAMPLES

Example 1

It may be convenient to prepare Fibrinin by separate reduction and blocking steps. Human fibrinogen is prepared as a solution (2% in 0.3 M NaCl) and dialyzed against 100 volumes of TNE-buffer (Tris-saline-EDTA buffer: 0.05 M Tris(hydroxymethyl)aminomethane, 0.1 M NaCl, 1 mM ethylenediaminetetraacetic acid, pH 7.4) during 3 hours with 3 changes of outer fluid. Any fibronectin present may be removed by affinity chromatography on gelatin-SEPHAROSE (agarose). The fibrinogen stock solution (about 12 mg/mL) is stored at −70° C. until used. Fibrinogen concentration is measured spectrophotometrically in alkaline urea (40% urea in 0.2N NaOH) using E (1%, 1 cm)= 1.65 at 282 nm.

Fibrinogen stock solution is diluted with TNE-buffer to a final concentration of 7 mg/mL and then DTT is added from a concentrated stock solution in water to 5 mM (final molarity). Nitrogen is blown over the sample and the tube is sealed and placed in a water bath at 37° C. for the duration of the reduction (45 minutes). The DTT is removed from the sample by gel filtration. For samples up to 1 mL volume a PD-10 column (Pharmacia, Piscataway, N.J.) can be used. The gel filtration column is equilibrated with nitrogen-saturated TNE-buffer. The protein is collected at a predetermined elution volume, the pH of the eluate is adjusted to 8.1 by the addition of 2M Tris, pH 8.5, and iodoacetic acid (Sigma, St. Louis Mo., recrystallized three times from petroleum ether before use) is added to give a final molarity of 1.6 mM. The iodoacetic acid stock solution (12 mM) is made in 0.1 N NaOH. Nitrogen is blown over the sample and the tube is sealed and kept in the dark at room temperature for 45 minutes. Afterwards, unreacted reagent is removed by gel filtration (columns equilibrated in TNE-buffer) or by dialysis against 400 to 1000 volumes of TNE-buffer during 3 hours with 3 changes of outer fluid, or by any other suitable means, such as by precipitating the protein and resolubilizing the protein in a suitable buffer, such as TNE-buffer.

The recovered partially reduced and alkylated fibrinogen is diluted to 3 mg/mL with TNE-buffer and treated with thrombin (human, purified from plasma, or obtained commercially) at 0.5 NIH units/mL for 2 hours at room temperature to release the amino terminal segments of the Aα- and Bβ-chains. The reaction is stopped by the addition of the thrombin inhibitor hirudin (Pentapharm, Basel, Switzerland) at a concentration of 2 to 7 ATU/mL.

Example 2

It may also be convenient to prepare Fibrinin by consecutive reduction and alkylation. Fibrinogen stock solution is diluted with TNE-buffer to a final concentration of 7 ml/mL and then DTT is added (from a concentrated stock solution in water) to 5 mM final molarity. Nitrogen is blown over the sample and the tube is sealed and placed in a water bath at 37° C. for the duration of the reduction (45 minutes). The pH of the sample is adjusted to 8.1 by the addition of 2M Tris, pH 8.5 and iodoacetic acid (Sigma, St. Louis, Mo., recrystallized three times from petroleum ether before use) is added to give a final molarity of 20 to 30 mM. The iodoacetic acid stock solution (500 mM) is made in 0.1 N NaOH. Nitrogen is blown over the sample and the tube is sealed and kept in the dark at room temperature for 45 minutes. Afterwards, unreacted reagents are removed by either gel filtration (columns equilibrated in TNE-buffer) or by dialysis against 400 to 2000 volumes of TNE-buffer during 4 to 20 hours with 3 to 4 changes of outer fluid, or any other suitable means.

The recovered partially reduced and alkylated fibrinogen is diluted to 3 mg/mL with TNE-buffer and treated with thrombin (human, purified from plasma, or obtained commercially) at 0.5 NIH units/mL for 2 hours at room temperature to release the amino terminal peptides. The reaction is stopped by the addition of the thrombin inhibitor hirudin at a concentration of 2 to 7 ATU/mL.

Example 3

It may be convenient to prepare the reduced and alkylated fibrinogen as described in Examples 1 and 2 and to treat the material with thrombin and later remove the enzyme from the reaction mixture by passing the sample over columns containing either insolubilized hirudin or high-avidity anti-thrombin antibody. The thrombin will bind to the column and only the Fibrinin will elute as pure material.

Example 4

It may be convenient to prepare Fibrinin complexes of high molecular weight, e.g., aggregates of several Fibrinin molecules covalently cross-linked together, that still retain full solubility and stability in normal physiological buffers and conditions as does monomeric Fibrinin. It may also be convenient to prepare high molecular weight complexes of material from the Fibrinin preparation protocols that has not been treated to remove the amino-terminal peptides, i.e., not treated with thrombin. These types of high molecular weight samples can be prepared by inducing the formation of covalent cross-linkages between particular glutamine and lysine residues in adjacent Fibrinin or Fibrinin-like monomers in solution by exposure of the solution to activated plasma factor XIII for a fixed time period.

The material from either Example 1, 2 or 3 is diluted with TNE-buffer to 0.5 to 10 mg/mL, with a suitable concentration being 1 mg/mL. Hirudin is added to the solution from a concentrated stock solution to a final concentration of 2–10 ATU/mL, with 8 ATU/mL being the preferred concentration. Calcium is then added to the solution from a 1 M concentrated stock solution of calcium chloride to a final concentration of 20 mM. Thrombin-activated factor XIII is then added to the sample to a final concentration of between 0.1 to 1 U per mL, with the optimum being 0.4 U/mL. The cross-linking reaction is allowed to proceed at room temperature for 30 to 90 minutes, with 60 minutes being preferred. The progress of the cross-linking can be followed spectrophotometrically at 350 nm. The absorbance should not change very much during the reaction. The reaction is stopped by the addition of a factor XIII inhibitor such as iodoacetamide, iodoacetic acid or others. This can be done by adding iodoacetamide (500 mM stock, freshly prepared in any neutral buffer) to a final concentration of 5 mM.

The activated factor XIII used for the cross-linking reaction is prepared beforehand by introducing thrombin to a stock solution of factor XIII for a period of 30 to 60 minutes, and then blocking the thrombin activity with an excess of hirudin, for example, see Blombäck, B., Procyk, R., Adamson, L. and Hessel, B., (1985), "FXIII Induced Gelation of Human Fibrinogen—An Alternative Thiol Enhanced, Thrombin Independent Pathway", *Thromb. Res.,* 37, 613–628). Briefly, this can be done by adding thrombin (4 units/mL) to a stock of factor XIII (at 8 U/mL) for 45 minutes at room temperature and stopping the activation process by addition of hirudin at 16 ATU/mL.

Example 5

Fibrinin, prepared as described in Examples 1–3 is useful as a fibrin standard for classical indirect binding ELISA or indirect competition ELISA. Wells of a polyvinyl microtiter plate (Costar, Cambridge, Mass.) are coated with 0.1 mL of either acid solubilized fibrin (4 mg/mL fibrin stock solution in 10% acetic acid, diluted to 8 μg/mL with 50 mM sodium carbonate buffer, pH 9.6) or the Fibrinin prepared as in Examples 1–3 (1 to 3 mg/mL stock solution, diluted to 8 μg/mL with 50 mM sodium carbonate buffer, pH 9.6). Coupling time is usually overnight at 4° C.

The antifibrin monoclonal antibody T2G1, is a suitable reagent for such indirect assays. Antibody T2G1 is an $IgG_{1k}$ that does not react with either fibrinogen or fibrin I (Kudryk, B., Rohoza, A., Ahadi, M., Chin, J., Wiebe, M. E. (1984) "Specificity of a Monoclonal Antibody for the $NH_2$-terminal Region of Fibrin", *Mol. Immunol.,* 21, 89–94). Antibody T2G1 reacts with thrombin-treated amino-terminal CNBr-fragment of human fibrinogen ((T)N-DSK), monomeric peptides Bβ15–21, Bβ15–42, Bβ15–118, Bβ15–461, as well as intact fibrin II (des AABB-fibrin). The antibody is diluted in TNE-buffer additionally containing 1 mg/mL bovine serum albumin (Sigma, St. Louis, Mo.) and 0.01% sodium azide so as to give an $A_{490}$/10 minutes value of 1.0–2.0 (see below). In the indirect ELISA, half of this concentration of antibody is incubated in the wells of the coated plate. Specifically bound antibody is detected with a peroxidase-conjugated rabbit antibody directed against mouse immunoglobulins (DAKO Corp., Santa Barbara, Calif.). FIG. 1 shows that different dilutions of the antifibrin monoclonal antibody bind to wells coated with the acid solubilized fibrin and also to wells coated with the soluble fibrin preparation described in this application.

FIG. 1 depicts the results of microtiter plate wells coated with either 2,350 fmol acid soluble fibrin (◙) or 2,350 fmol Fibrinin prepared as described in Example 3 (♦). Indirect binding ELISA was done using 9.6–611 fmol T2G1 antibody per well. Specifically bound antibody on the plastic wells were detected with a peroxidase-conjugated rabbit antibody directed against mouse immunoglobulins, $H_2O_2$ and o-dianisidine.

Figure 2:
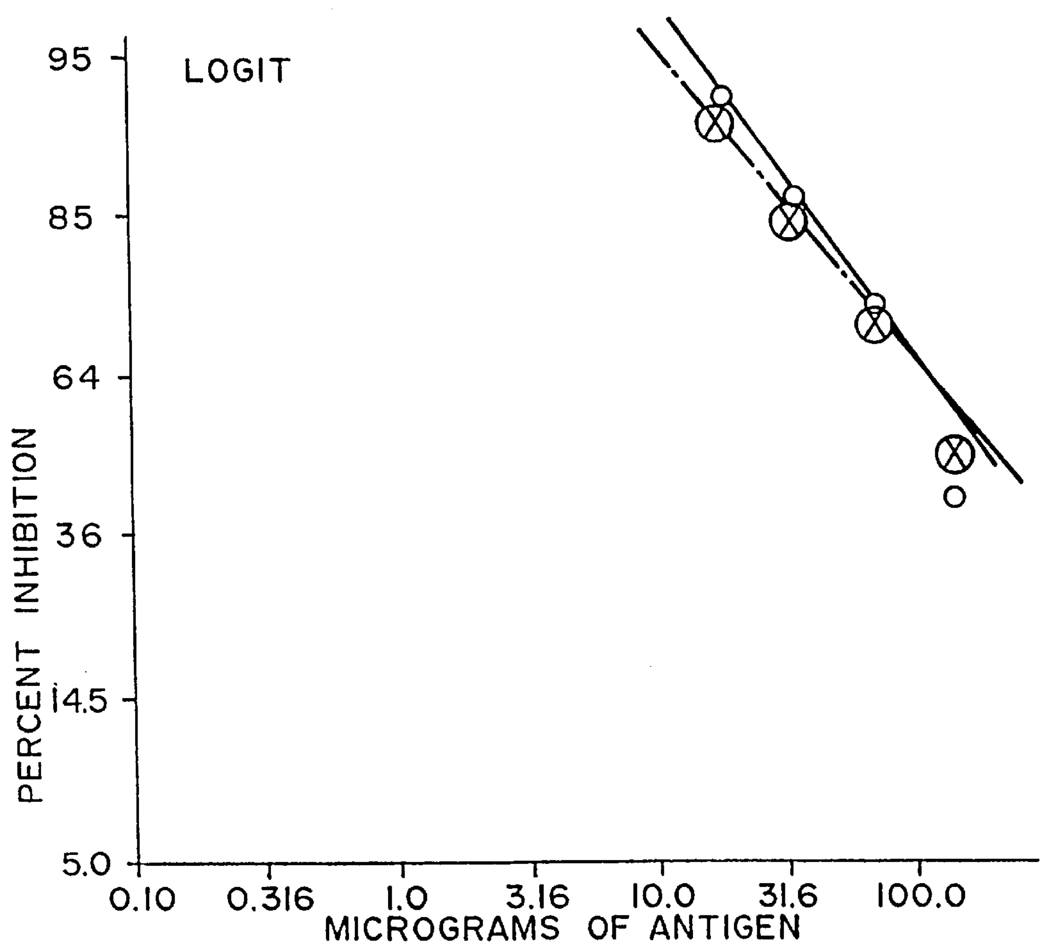
FIG. 2 is a graph depicting the relationship between the inhibition of anti-fibrin antibody binding to plastic wells coated with either acid solubilized fibrin or the soluble fibrin-like monomer produced according to the invention and the concentration of antigen (i.e., soluble fibrin-like monomer produced according to the invention) added to the antibody sample.

For the indirect competition ELISA using the antifibrin antibody T2G1, a standard curve is obtained by mixing the dilution of antibody with dilutions (2–40 picomole per mL) of Fibrinin prepared as described in Example 3. The mixtures are allowed to come to equilibrium (usually for 2 hours, room temperature) and then added to the plate. Specifically bound antibody in the plastic wells is detected with a peroxidase-conjugated rabbit antibody directed against mouse immunoglobulins (DAKO Corp. Santa Barbara, Calif.). FIG. 2 shows that a suitable standard curve is obtained by this protocol.

FIG. 2 depicts ELISA the results using microtiter plates coated with either 8 g/mL acid soluble fibrin (⦿) or 8 μg/mL Fibrinin prepared as described in Example 3 (⊗). Indirect competition ELISA was conducted using a constant amount of T2G1 antibody (6.1 pmol/mL) reacting with serially diluted Fibrinin prepared as described in Example 3 (2.5 to 20 pmol/mL). Specifically bound antibody on the plastic wells was detected with a peroxidase-conjugated rabbit antibody directed against mouse immunoglobulins, $H_2O_2$ and o-dianisidine.

The soluble fibrin-like preparation, Fibrinin, can also be employed for any type of ELISA involving monoclonal antibodies with specificities for particular conformational epitopes of the soluble Fibrinin which it may share with fibrin II prepared directly from fibrinogen or for any assay which requires soluble fibrin monomers as a reagent, some of which are illustrated below.

Example 6

The soluble fibrin prepared as described in this invention is also useful in RIA for determining the concentration of soluble fibrin monomer or fibrin degradation products in plasma or related samples to which suitable antibodies that also react with Fibrinin are available. The assay is carried out under RIA competitive binding conditions in the usual manner, for example, as described in Harlow, E. and Lane, D. (1988), *Antibodies. A Laboratory Manual.* Cold Spring Harbor Laboratory, the entire contents of which are incorporated by reference herein. Basically, this involves adding a sufficient amount of an antibody directed against fibrin, such as the T2G1 antibody mentioned in Example 5, and radioactively labelled Fibrinin prepared as described in Example 3, to the plasma or related sample, thereafter separating antibody bound radiolabeled Fibrinin, soluble fibrin and or related fibrin degradation products from unbound species and measuring the radioactivity of the bound fraction.

Any method for radiolabeling Fibrinin may be used. Conveniently, $^{125}I$ can be introduced into any protein-containing tyrosyl or histidyl moieties (Fibrinin is one such protein) by either chemical (Chloramine-T) or enzymatic (lactoperoxidase) methods. A detailed procedure for preparing labeled fibrinogen which can also be used to prepare the Fibrinin that is described in this invention may be found in Procyk, R, Adamson, L., Block, M. & Blombäck, B. (1985), "Factor XIII Catalyzed Formation of Fibrinogen-Fibronectin Oligomers—A Thiol Enhanced Process". *Thromb. Res.,* 40, 833–852. Alternatively, a radiolabeled blocking reagent, such as $^{3}H$- or $^{14}C$- labeled iodoacetic acid, may be used in the blocking step of the process of preparing the soluble Fibrinin described in Examples 1 and 2. A detailed procedure for this preparation may be found in Procyk, R. & Blombäck, B., (1990), "Disulfide Bond Reduction in Fibrinogen: Calcium protection and Effect on Clottability", *Biochemistry,* 29, 1501–1507, the entire contents of which are incorporated by reference herein.

Generally, the Fibrinin prepared as described in this invention is labeled with I-125 (or other radioisotopes) to specific activities of 10 to 100 μCi/mg depending on the isotope used. The radiolabeled soluble Fibrinin may be diluted with suitable aqueous buffers as is known in the art to provide optimum assay sensitivity.

After the unknown sample of plasma or sample containing fibrin degradation product has been mixed with the radioactively labeled Fibrinin, an antibody capable of immunoreactivity with the soluble fibrin or fibrin degradation products and the radioactive Fibrinin prepared as described in this invention, is added to the mixture. The antibody has a specificity for both of the above components, thus, the quantity of radioactive Fibrinin bound by a given quantity of antibody is decreased in the presence of unlabeled soluble fibrin or fibrin degradation products.

Upon completion of the incubation step, the unbound Fibrinin, soluble fibrin or fibrin degradation products are separated from the antibody bound material by any one of the usual methods, e.g., agarose bead-coupled second antibody to the first antibody which has no specificity to Fibrinin, soluble fibrin or fibrin degradation products. The radioactivity of the bound complexes are determined and used to relate to the amount of soluble fibrin or fibrin degradation products in the sample, as is usually done in any standard RIA.

Example 7

Fibrinin, prepared as described in this application, can also be utilized as a standard for the determination of fibrin monomer concentration in plasma samples. Commercially available kits for the photometric determination of fibrin monomer in plasma, such as the COA-SET$^R$ fibrin monomer kit marketed by Kabi Diagnostica (Molndal, Sweden), are based on the principal that the enzyme plasminogen is converted to plasmin by tissue plasminogen activator (t-PA) and the activation rate of the conversion is enhanced in the presence of soluble fibrin monomers. The amount of fibrin monomer in a plasma sample is determined by measuring the amidolytic activity of the plasmin generated, since this will be proportional to the extent of the enhancement of t-PA's ability to convert plasminogen to plasmin. The chromogenic substrate S-2390 (Kabi Diagnostica, Molndal, Sweden) is used since plasmin will cause the release of the p-nitroaniline group, which leads to a change in absorbance at 405 nm.

Figure 3:
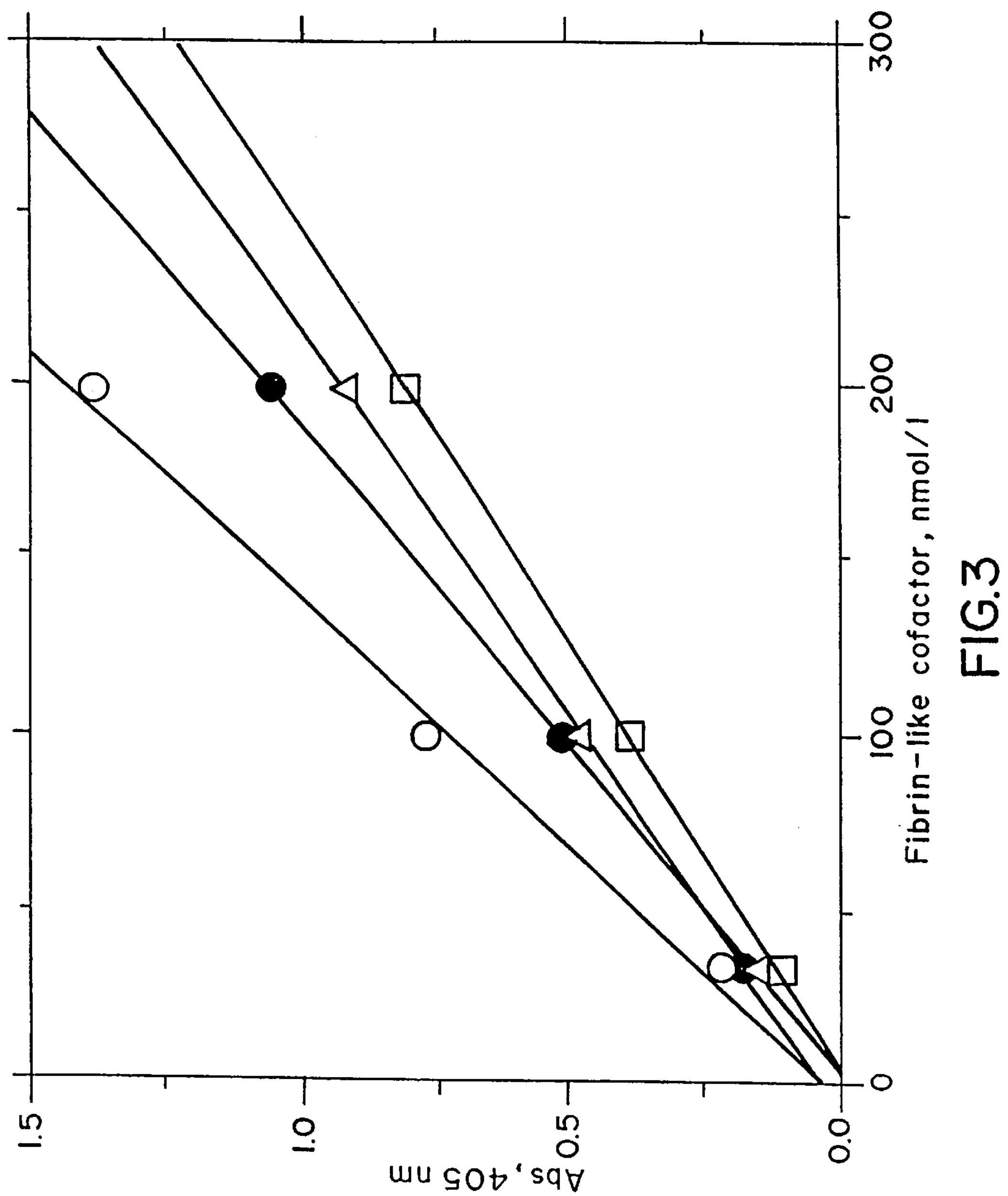
FIG. 3 is a plot of absorbance for different concentrations of the standards used in a fibrin monomer assay.

The calibration standards provided with the COA-SET$^R$ fibrin monomer kit were tested along with identical concentrations of Fibrinin prepared as described in Example 3 (FIG. 3). The slopes of the two standard curves were similar, with Fibrinin prepared as described in Example 3 being useful in the 30–200 nanomole per liter plasma concentration range of fibrin monomer.

FIG. 3 is a plot of absorbance of the standards used in the fibrin monomer assay. Fibrin monomer standard supplied with the COA-SET$^R$ Fibrin monomer kit (□) soluble Fibrinin prepared as described in Example 2 (Δ); soluble Fibrinin prepared as described in this application in Examples 2 and 3 (●); DESAFIB™ des-AA-fibrinogen (American Diagnostica Inc.) (○). The fibrin monomer standard supplied with the COA-SET$^R$ fibrin monomer kit comes in lyophilized form and upon rehydration according to manufacturer's instructions sometimes contains some particulate matter. The soluble Fibrinin prepared as described in this invention had no such problems of solubility. The entire assay is conducted in the presence of plasma, as instructed by the manufacturer, and shows that the soluble Fibrinin prepared as described in the application can be applied to such assays in the presence of plasma.

Example 8

Figure 4:
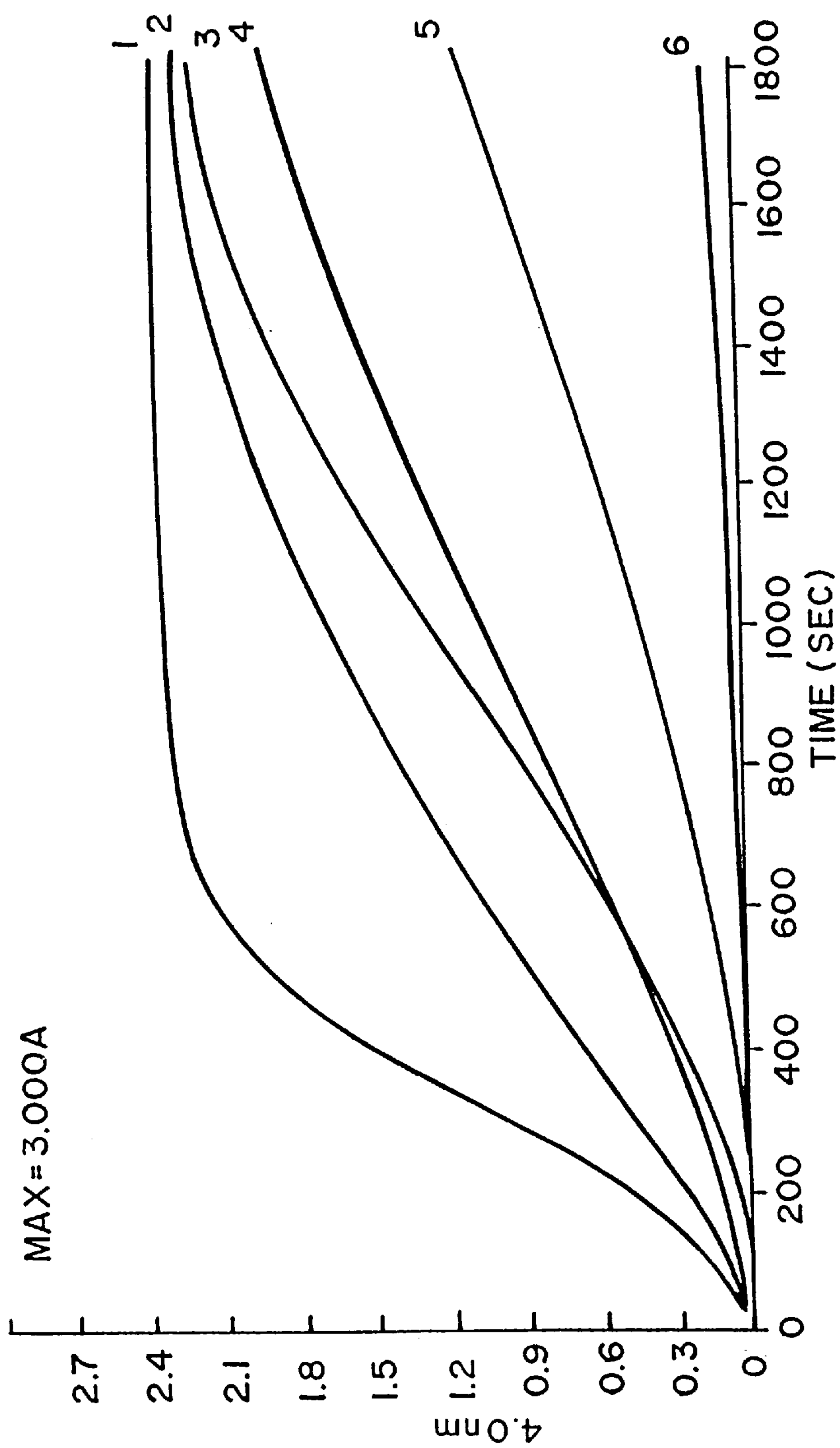
FIG. 4 is a plot of the development of absorbance representing the amidolytic activity of plasmin generated through hydrolysis of chromogenic substrate S-2251 in the presence of various stimulators.

The soluble Fibrinin prepared as described in this application is also useful for the determination of t-PA activity in human plasma. The assay routinely used is based on the amidolytic activity of the amount of plasmin generated. The activity of t-PA requires the presence of t-PA stimulator, and the soluble fibrin-like material, Fibrinin, prepared as described in this application is a very suitable substitute for the commercially available preparations. As seen in FIG. 4, Fibrinin prepared as described in this application gave maximum t-PA stimulation, much higher than DESAFIB™ (des-AA-fibrinogen) (American Diagnostica, Inc., Greenwich, Conn.) or fibrin monomer standard (Kabi Diagnostica, Molndal, Sweden).

FIG. 4 is a plot of the development of absorbance representing the amidolytic activity of plasmin generated through hydrolysis of chromogenic substrate S-2251. The conversion of plasminogen to plasmin was carried out in the presence of t-PA and different t-PA stimulators: soluble Fibrinin prepared as described in Examples 2 and 3 (curve 1); fibrin monomer standard supplied with the COA-SET$^R$ fibrin monomer kit (curve 2); soluble, partially reduced and alkylated fibrinogen prepared as described in the application, except omitting the thrombin digestion step (curve 3); DESAFIB™ (American Diagnostica Inc.) (curve 4); plasminogen-free fibrinogen (IMCO, Stockholm, Sweden) (curve 5); no t-PA stimulator (curve 6). The final concentrations of the components in the assay was as follows: plasminogen (0.22 μM); S-2251 (0.45 mM); tPA (33 U/mL); stimulator (0.1 mg/mL). The assay buffer was 63 mM Tris, pH 8.5, 0.01% "TWEEN 80".

Example 9

Various modified preparations of Fibrinin or Fibrinin-like material can be used for stimulating t-PA activity, as in Example 8.

Figure 5:
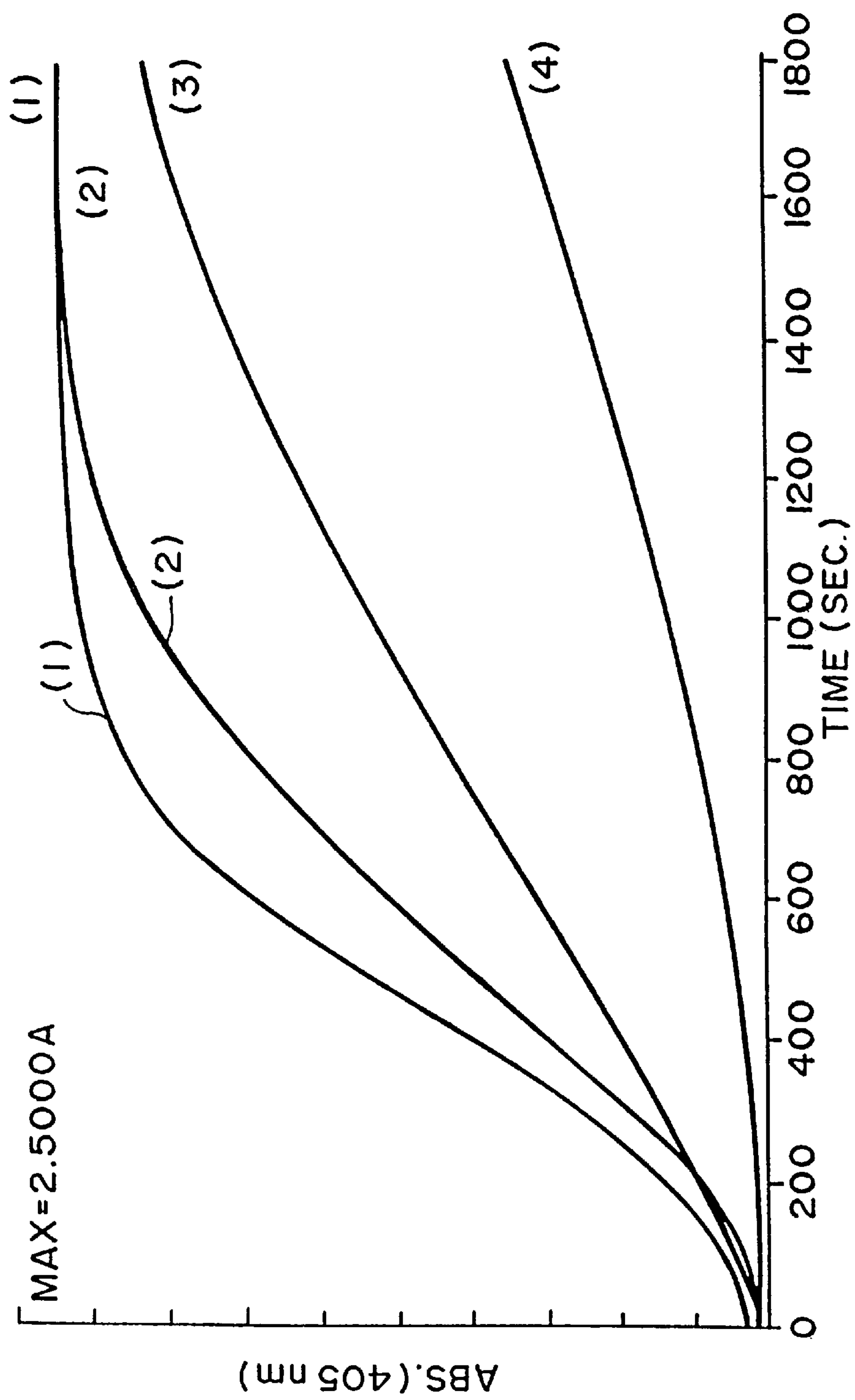
FIG. 5 is a plot similar to FIG. 4, but for various crosslinked stimulators.

FIG. 5 is a plot of absorbance representing the amidolytic activity of plasmin generated through hydrolysis of chromogenic substrate S-2251. The conversion of plasminogen to plasmin was carried out in the presence of t-PA and different cross-linked t-PA stimulators: soluble Fibrinin prepared as described in Example 4 as a high molecular weight complex (curve 1); soluble Fibrinin prepared as described in Example 3 (curve 2); plasminogen-free fibrinogen that has been cross-linked by factor XIII under identical conditions as called for in Example 4 (curve 3); plasminogen-free fibrinogen (curve 4). It is evident that the cross-linked samples gave higher stimulatory activity in every case.

It will be appreciated that the instant specification is set forth by way of illustration and not limitation, and that various modifications and changes may be made without departing from the spirit and scope of the present invention.

What is claimed is:

1. In an assay for determining all unknown fibrin monomer concentration in a first plasma sample, said assay comprising contacting said first plasma sample with plasminogen, tissue plasminogen activator, a substrate which undergoes a color change when plasmin is generated, and after a suitable incubation period correlating any color change to that undergone by a second plasma sample containing fibrin monomer of a known concentration to give an indication of the fibrin monomer concentration in said first plasma sample, wherein the improvement, comprises the fibrin monomer of known concentration in said second plasma is a modified fibrinogen, the modified fibrinogen obtained by a process comprising the following steps: partially reducing 3 to 25 micromolar fibrinogen with 0.25 millimole per nanomole of said fibrinogen with a reducing agent at 30–40° C. under non-denaturing conditions in the absence of divalent cations for 0.5 to 1.5 hours, then (2) blocking thiol groups of any free cysteines formed during step (1) by reacting the product of step (1) with a blocking agent that does not cause precipitation of the product of step (2), then (3) reacting the product of step (2) with a clotting enzyme in a physiological buffer in the absence of divalent cations to release fibrinopeptides A and B, and (4) terminating the activity of said clotting enzyme.

2. In an assay for determining plasminogen activator inhibitor activity, said assay comprising contacting plasma containing an unknown concentration of plasminogen activator inhibitor activity with a soluble fibrin or fibrin monomer reagent, and a known concentration of tissue plasminogen activator, and after a suitable incubation period calulating any residual tissue plasminogen activator concentration to give an indication of the plasminogen activator inhibitor activity in said plasma, wherein the improvement comprises using a modified fibrinogen as the soluble fibrin or fibrin monomer reagent, the modified fibrinogen obtained by a process comprising the following steps: (1) partially reducing 3 to 25 micromolar fibrinogen with 0–25 millimole per nanomole of said fibrinogen with a reducing agent at 30–40° C. under non-denaturing conditions in the absence of divalent cations for 0.5 to 1.5 hours, then (2) blocking thiol groups of any free cysteines formed during step (1) by reacting the product of step (1) with a blocking agent that does not cause precipitation of the product of step (2), then (3) reacting the product of step (2) with a clotting enzyme in a physiological buffer in the absence of divalent cations to release fibrinopeptides A and B, and (4) terminating the activity of said clotting enzyme.

3. In an assay for determining tissue plasminogen activator activity, said assay comprising contacting a sample of unknown tissue plasmninogen activator activity with a soluble fibrin or fibrin monomer reagent, a substrate which undergoes a color change when plasmin is generated, and one of plasminogen, plasma or standard containing a known amount of tissue plasminogen activator, and after a suitable incubation period calculating any rate of color change to given an indication of the tissue plasminogen activator activity in said sample, wherein the improvement comprises using a modified fibrinogen as the soluble fibrin or fibrin monomer reagent, the modified fibrinogen obtained by a process comprising the following steps: (1) partially reducing 3 to 25 micromolar fibrinogen with 0.25 millimole per nanomole of said fibrinogen with a reducing agent at 30–40° C. under non-denaturing conditions in the absence of divalent cations for 0.5 to 1.5 hours, then (2) blocking thiol groups of any free cysteines formed during step (1) by reacting the product of step (1) with a blocking agent that does not cause precipitation of the product of step (2), then (3) reacting the product of step (2) with a clotting enzyme in a physiological buffer in the absence of divalent cations to release fibrinopeptides A and B, and (4) terminating the activity of said clotting enzyme.

4. In a competitive immunoassay for determining fibrin and fibrin degradation products in a sample, said immunoassay comprising individually contacting said sample and a positive control of known fibrin and fibrin degradation products concentration with a labelled antibody which specifically binds to said fibrin and fibrin degradation products, and after a suitable incubation period separating bound labelled antibody from unbound labelled antibody, measuring bound label, and comparing measured bound label in the contacted sample to measured bound label in the contacted positive control to determine the presence or amount of said fibrin and fibrin degradation products in said sample, wherein the improvement comprises using a modified fibrinogen as said fibrin and fibrin degradation products in said positive control, the modified fibrinogen obtained by a process comprising the following steps: (1) partially reducing 3 to 25 micromolar fibrinogen with 0.25 millimole per nanomole of said fibrinogen with a reducing agent at 30–40° C. under non-denaturing conditions in the absence of divalent cations for 0.5 to 1.5 hours, then (2) blocking thiol groups of any free cysteines formed during step (1) by reacting the product of step (1) with a blocking agent that does not cause precipitation of the product of step (2), then (3) reacting the product of step (2) with a clotting enzyme in a physiological buffer in the absence of divalent cations to release fibrinopeptides A and B, and (4) terminating the activity of said clotting enzyme.

5. In a competitive immunoassay for determining fibrin and fibrin degradation products in a sample, said immunoassay comprising individually contacting said sample and a positive control of known fibrin or fibrin monomer concentration with a first antibody which specifically binds to said fibrin, said fibrin degradation products and said fibrin monomer to form individual test reaction and control reaction mixtures; contacting an aliquot of each test reaction and control reaction mixture to a separate well, wherein each well is coated with the same concentration of said fibrin or fibrin monomer; removing any unbound first antibody from each well; contacting each well with a labelled anti-first antibody antibody; measuring any bound label in each well and comparing the measured bound label in the sample wells to the measured bound label in the positive control wells to determine the presence or amount of said fibrin and fibrin degradation products in the sample, wherein the improvement comprises using a modified fibrinogen as said fibrin or fibrin monomer in said positive control, the modified fibrinogen obtained by a process comprising the following steps: (1) partially reducing 3 to 25 micromolar fibrinogen with 0.25 millimole per nanomole of said fibrinogen with a reducing agent at 30–40° C. under non-denaturing conditions in the absence of divalent cations for 0.5 to 1.5 hours, then (2) blocking thiol groups of any free cysteines formed during step (1) by reacting the product of step (1) with a blocking agent that does not cause precipitation of the product of step (2), then (3) reacting the product of step (2) with a clotting enzyme in a physiological buffer in the absence of divalent cations to release fibrinopeptides A and B, and (4) terminating the activity of said clotting enzyme.

6. In a competitive immunoassay for determining fibrin and fibrin degradation products in a sample, said immunoassay comprising individually contacting said sample and a positive control of known fibrin or fibrin monomer concentration with a labelled antibody which specifically binds to said fibrin, said fibrin degradation products and said fibrin monomer to form individual test reaction and control reaction mixtures; contacting an aliquot of each test reaction and control reaction mixture to a separate well, wherein each well is coated with the same concentration of said fibrin or fibrin monomer; removing any unbound labelled antibody from each well; measuring any bound label in each well and comparing the measured bound label in the sample wells to the measured bound label in the positive control wells to determine the presence or amount of said fibrin and fibrin degradation products in the sample, wherein the improvement comprises using a modified fibrinogen as said fibrin or fibrin monomer in said positive control, the modified fibrinogen obtained by a process comprising the following steps: (1) partially reducing 3 to 25 micromolar fibrinogen with 0.25 millimole per nanomole of said fibrinogen with a reducing agent at 30–40° C. under non-denaturing conditions in the absence of divalent cations for 0.5 to 1.5 hours, then (2) blocking thiol groups of any free cysteines formed during step (1) by reacting the product of step (1) with a blocking agent that does not cause precipitation of the product of step (2), then (3) reacting the product of step (2) with a clotting enzyme in a physiological buffer in the absence of divalent cations to release fibrinopeptides A and B, and (4) terminating the activity of said clotting enzyme.

7. In a sandwich immunoassay for determining fibrin and fibrin degradation products in a sample, said immunoassay comprising coating wells of a microtiter plate with a first antibody which specifically binds to said fibrin, said fibrin degradation products and fibrin monomer; contacting said sample and a positive control of known fibrin or fibrin monomer concentration to separate wells of said microtiter plate; removing any unbound sample or positive control from its respective well; contacting each well with a labelled anti-first antibody antibody; measuring any bound label in each well and comparing the measured bound label in the sample wells to the measured bound label in the positive control wells to determine the presence or amount of said fibrin and fibrin degradation products in the sample, wherein the improvement comprises using a modified fibrinogen as said fibrin or fibrin monomer in said positive control, the modified fibrinogen obtained by a process comprising the following steps: (1) partially reducing 3 to 25 micromolar fibrinogen with 0.25 millimole per nanomole of said fibrinogen with a reducing agent at 30–40° C. under non-denaturing conditions in the absence of divalent cations for 0.5 to 1.5 hours, then (2) blocking thiol groups of any free cysteines formed during step (1) by reacting the product of step (1) with a blocking agent that does not cause precipitation of the product of step (2), then (3) reacting the product of step (2) with a clotting enzyme in a physiological buffer in the absence of divalent cations to release fibrinopeptides A and B, and (4) terminating the activity of said clotting enzyme.

* * * * *